United States Patent
Felding et al.

(10) Patent No.: US 10,780,186 B2
(45) Date of Patent: Sep. 22, 2020

(54) SYSTEM, APPARATUS, EQUIPMENT WITH THERMAL DISINFECTION AND THERMAL DISINFECTION METHODS

(71) Applicant: Gambro Lundia AB, Lund (SE)

(72) Inventors: Anders Felding, Limhamm (SE); Tor-Bjorn Jonasson, Lund (SE); Dan Jonsson, Svedala (SE); Rolf Nystrand, Malmo (SE)

(73) Assignee: Gambro Lundia AB, Lund (SE)

( * ) Notice: Subject to any disclaimer, the term of this patent is extended or adjusted under 35 U.S.C. 154(b) by 411 days.

(21) Appl. No.: 14/438,955

(22) PCT Filed: Nov. 13, 2013

(86) PCT No.: PCT/EP2013/073705
§ 371 (c)(1),
(2) Date: Apr. 28, 2015

(87) PCT Pub. No.: WO2014/082855
PCT Pub. Date: Jun. 5, 2014

(65) Prior Publication Data
US 2015/0273090 A1 Oct. 1, 2015

Related U.S. Application Data

(60) Provisional application No. 61/730,579, filed on Nov. 28, 2012.

(30) Foreign Application Priority Data

Nov. 28, 2012 (SE) ..................................... 1251349

(51) Int. Cl.
*A61L 2/04* (2006.01)
*A61L 2/24* (2006.01)
(Continued)

(52) U.S. Cl.
CPC .................. *A61L 2/04* (2013.01); *A61L 2/24* (2013.01); *A61M 1/1686* (2013.01);
(Continued)

(58) Field of Classification Search
None
See application file for complete search history.

(56) References Cited

U.S. PATENT DOCUMENTS 3,809,241 A 5/1974 Alvine
4,018,684 A 4/1977 Uffer
(Continued)

FOREIGN PATENT DOCUMENTS

DE 2934167 3/1981
DE 3447989 1/1986
(Continued)

OTHER PUBLICATIONS

DE 19655227 Machine Translation.pdf—Aug. 27, 2009—Aksys, LTD (corresponds to Foreign Cite No. 2 on IDS dated Apr. 28, 2015).*
(Continued)

*Primary Examiner* — Bradley R Spies
(74) *Attorney, Agent, or Firm* — K&L Gates LLP

(57) ABSTRACT

Water systems, medical equipment, and apparatus for thermal disinfection comprise a control unit which starts the disinfection of a fluid path by controlling a heating unit to heat water and controlling an actuator to enable heated water to flow into the fluid path. The control unit reads the temperature as measured by a temperature sensor during the disinfection and calculates an achieved disinfection dose. The achieved disinfection dose is compared with a set disinfection dose and the disinfection is discontinued if the achieved disinfection dose corresponds to the set disinfection dose.

23 Claims, 6 Drawing Sheets

(51) Int. Cl.
    *A61M 1/16*     (2006.01)
    *C02F 1/00*     (2006.01)
    *C02F 1/02*     (2006.01)
    *C02F 103/02*   (2006.01)
    *G05B 15/02*    (2006.01)
    *G05D 7/06*     (2006.01)

(52) U.S. Cl.
    CPC ........... *A61M 1/1688* (2014.02); *C02F 1/008* (2013.01); *C02F 1/02* (2013.01); *G05B 15/02* (2013.01); *G05D 7/0629* (2013.01); *A61M 2205/3368* (2013.01); *A61M 2205/36* (2013.01); *C02F 2103/026* (2013.01); *C02F 2209/02* (2013.01); *C02F 2209/44* (2013.01); *C02F 2301/046* (2013.01); *C02F 2303/04* (2013.01)

(56) References Cited

U.S. PATENT DOCUMENTS

| | | | |
|---|---|---|---|
| 4,153,554 | A | 5/1979 | von der Heide et al. |
| 4,683,053 | A | 7/1987 | Polaschegg |
| 4,789,467 | A | 12/1988 | Lindsay et al. |
| 5,591,344 | A | 1/1997 | Kenley et al. |
| 5,651,893 | A | 7/1997 | Kenley et al. |
| 5,895,578 | A | 4/1999 | Simard et al. |
| 6,051,188 | A | 4/2000 | Spickermann et al. |
| 6,579,494 | B1 | 6/2003 | Chevallet et al. |
| 8,562,834 | B2 | 10/2013 | Kamen et al. |
| 2004/0079700 | A1 | 4/2004 | Wood et al. |
| 2004/0215129 | A1 | 10/2004 | Edgson et al. |
| 2005/0002824 | A1 * | 1/2005 | Halli ............... A61L 11/00 422/3 |
| 2005/0171501 | A1 | 8/2005 | Kelly |
| 2006/0291839 | A1 | 12/2006 | Yano |
| 2007/0102357 | A1 | 5/2007 | Weatherill |
| 2009/0134080 | A1 | 5/2009 | Fabig |
| 2009/0206017 | A1 | 8/2009 | Rohde et al. |
| 2010/0192686 | A1 | 8/2010 | Kamen et al. |
| 2010/0263687 | A1 | 10/2010 | Braun et al. |
| 2011/0192796 | A1 | 8/2011 | Smejtek et al. |
| 2012/0308431 | A1 | 12/2012 | Kotsos et al. |
| 2013/0126430 | A1 | 5/2013 | Kenley et al. |
| 2014/0098627 | A1 | 4/2014 | Mochizuki et al. |
| 2014/0276373 | A1 | 9/2014 | Minkus |

FOREIGN PATENT DOCUMENTS

| | | | |
|---|---|---|---|
| DE | 10013964 | 9/2001 | |
| DE | 10310418 | 9/2004 | |
| DE | 19655227 | 8/2009 | |
| EP | 0428009 | 5/1991 | |
| EP | 1236685 | 9/2002 | |
| FR | 2864530 A1 * | 7/2005 | ......... F24D 17/0073 |
| JP | 2004049977 | 2/2004 | |
| JP | 2009056271 | 3/2009 | |
| JP | 2010194092 | 9/2010 | |
| JP | 2011-125863 A | 6/2011 | |
| WO | 9609080 | 3/1996 | |
| WO | 96/25214 | 8/1996 | |
| WO | 9640313 | 12/1996 | |
| WO | 00/57928 | 10/2000 | |
| WO | 00/57935 | 10/2000 | |
| WO | 2012119799 | 9/2012 | |
| WO | 2012/166377 | 12/2012 | |

OTHER PUBLICATIONS

Navarro et al—FR-2864530-A1 English Abstract (Year: 2005).*
International Search Report PCT/EP2014/078401—dated Apr. 1, 2015—4 pages.
Written Opinion of the International Searching Authority PCT/EP2014/078401—dated Apr. 1, 2015—8 pages.
Search Report for International Patent Application PCT/EP2014/074236 dated Jan. 21, 2015 (4 pages).
Written Opinion for International Patent Application PCT/EP2014/074236 dated Jan. 21, 2015 (6 pages).
International Search Report and Written Opinion dated Feb. 4, 2014, for related International Appln. No. PCT/EP2013/073705.
Rosenberg, "Thermal Disinfection—The A0 Concept and the Biological Background", 2003, vol. 11, pp. 118-119.
BSI; International Organization for Standardization; "Washer-disinfectors—Part 1: General requirements, terms and definitions and tests"; ISO 15883-1:2006; BS EN ISO 15883-1:2009; Oct. 31, 2009—84 Pages.
BSI; International Organization for Standardization; "Guidance for the preparation and quality management of fluids for haemodialysis and related therapies"; BS ISO 23500:2011; May 15, 2011—94 Pages.
ESRD; Centers for Medicare and Medicaid Services; "ESRD Surveyor Training: Interpretive Guidance"; Final Version 1.1; Oct. 3, 2008—304 Pages.
Ragon, Alain, et al. "Microbiological Evaluation of the Efficiency Hot RO Water Only Used to Disinfect Hemodialysis Water Distribution Loop in Operation for 5 Years." European renal Association, Clin Kidney J 4 (2011). 1 Page.
European Opposition dated Dec. 6, 2019 by Clemens Bauer against related European Patent 2 925 383 (13794846.9) Systems, Apparatus, Equipment With Thermal Disinfection and Thermal Disinfection Methods.

* cited by examiner

SYSTEM, APPARATUS, EQUIPMENT WITH THERMAL DISINFECTION AND THERMAL DISINFECTION METHODS

CROSS-REFERENCE TO RELATED APPLICATIONS

The present application is a National Phase of International Application No. PCT/EP2013/073705, filed on Nov. 13, 2013, which claims priority to Swedish Patent Application No. 1251349-5, filed Nov. 28, 2012, and U.S. Provisional Application No. 61/730,579, filed Nov. 28, 2012, the entire contents of each of which is incorporated herein by reference.

TECHNICAL FIELD

The invention relates to water systems, medical equipment (such as dialysis apparatus), and apparatus for thermal disinfection and methods for thermal disinfection.

BACKGROUND

There are several types of treatments in which blood is extracted in an extracorporeal blood circuit. Such treatments involve, for example, haemodialysis, haemofiltration, haemodiafiltration, plasmapheresis, blood component separation, blood oxygenation, etc. Normally, blood is removed from a blood vessel at an access site and returned to the same blood vessel or at another location in the body.

In the case of haemodialysis, a treatment fluid (also referred to as a dialysis fluid) is made approximately isotonic with a patient's blood. The treatment fluid and the patient's blood are made to flow on each side of a semi-permeable membrane of a membrane device (referred to as a dialyzer). Diffusive transfer is achieved from one side of the membrane to the other when the concentration of the substance on each side of the membrane differs. Such substances may be impurities in the blood (urea, creatinine, etc.) which thereby migrates from the blood to the treatment fluid. In treatment by haemodiafiltration, a convective transfer by ultrafiltration, resulting from a pressure difference created between the blood side and the treatment fluid side of the membrane, is added to the diffusive transfer.

An apparatus for extracorporeal blood treatment includes a stage in which the disposable extracorporeal blood circuit is coupled to a treatment control monitor (e.g. dialysis apparatus). This stage, which is prepared before connecting up the extracorporeal blood circuit to the patient, includes connection of the blood transport lines (in general an arterial line for blood removal from the patient, and a venous line for blood return to the patient) to the membrane device for blood treatment, which in turn is connected up to the treatment fluid supply circuit and to a used treatment fluid discharge circuit.

The semi-permeable membrane of the membrane device divides a blood compartment, connected to the blood transport lines, and a fluid compartment, connected to the supply and discharge circuits. The blood transport lines are further coupled to a sensor and actuator system equipped on the treatment control monitor, which system normally comprises means for blood circulation, pressure sensors, air bubble sensor, one or more circuit blocking clamps, blood detector, etc.

The treatment fluid supply circuit receives water from a water system. The water system may be a small unit providing water to only a single treatment control monitor but may also be a large unit providing water by means of a water system loop arrangement to a significant number of treatment units in for example a hospital or a clinic.

A large amount of water is required during dialysis treatment. Dialysis fluid, which may come into contact with the patients' blood, is often prepared from the water by means of a treatment fluid supply circuit. In for example haemodiafiltration fluid exchange takes place and replacement fluid (for example from the treatment fluid supply circuit) is entered into the patient's circular system. For this reasons, it is of paramount importance that the water used for the treatment is free from undesired ions, bacteria and their residue and degradation products, such as endotoxins.

The water system may be disinfected by a chemical process (e.g. using NaOCl or other chemical disinfection agents) in order to reduce the presence of bacteria in the water system. Chemical disinfection is an efficient way to reduce the presence of bacteria but it makes great demands on the following rinse procedure and requires very close measuring to assure that the water system is free from chemical residual products before being used for treatments. The chemical process is not environmentally friendly and may have a negative effect on the life-length of the disinfected parts and components.

In an alternative disinfection process, thermal disinfection is achieved by circulating hot water in the fluid system. As a result, the problem of chemical residual products does not exist, the process puts less load on the environment, and has comparatively less negative effect on the life-length of the disinfected parts and components.

Thermal disinfection processes are often carried out during the nights when there are no patients to treat. However, as the number of dialysis patients increases, it is becoming more usual in the dialysis clinics to have staff working in two or three shifts per 24 hours. The efficient treatment time for a treatment may be 5 hours with an additional 1-2 hours for preparing and finalizing the treatment. Consequently, the available time for disinfection is just a few hours when the staffs are working in three shifts.

The disinfection of the dialysis apparatus may be performed with use of the hot water provided by the water system during the thermal disinfection process of the water system.

SUMMARY

According to an aspect of the present invention there is provided a water system for providing water to at least one connected device through a fluid path and being able to disinfect the fluid path by means of thermal disinfection, the Water System comprising an inlet for receiving water to the water system, a heating unit configured to heat water within the water system, a filter unit configured to filter water within the water system in order to provide filtered water to an outlet, an actuator configured to control the flow of the water from the heating unit to the outlet, a fluid path connected to the outlet, the fluid path comprising at least one connector configured to connect to at least one device to which water is provided by the Water System, a temperature sensor located at the fluid path and configured to measure the temperature of the fluid in the fluid path, a control unit connected to the heating unit, the actuator and the temperature sensor, the control unit being configured to control the flow of water by means of the actuator, to control the heating of water by means of the heating unit, and to read the temperature as measured by the temperature sensor, and that the control unit is configured to start the disinfection of the fluid path by controlling the heating unit to heat water and controlling the actuator to enable heated water to flow to the outlet and further into the fluid path, and the control unit is configured to read the temperature as measured by the temperature sensor during the disinfection, and to calculate an achieved disinfection dose, and to compare the achieved disinfection dose with a set disinfection dose, and to discontinue the disinfection if the achieved disinfection dose at least corresponds to the set disinfection dose.

According to another aspect of the present invention there is provided medical equipment comprising a fluid path, the fluid path at least partly consisting of a fluid path with a need for regular disinfection, the medical equipment further comprising an inlet adapted to receive fluid, an actuator configured to control the flow of the fluid from the inlet to a connector, the connector being configured to connect to the fluid path with a need for regular disinfection, a temperature sensor configured to measure the temperature of the fluid in the fluid path, a control unit connected to the actuator and the temperature sensor, the control unit being configured to control the fluid flow by means of the actuator, and to read the temperature measured by the temperature sensor, and that the control unit is configured to receive and/or retrieve a set disinfection dose, and the control unit is configured to start the disinfection of the fluid path to be disinfected by controlling the actuator to enable fluid from the inlet to flow to the connector and further into the fluid path with a need for regular disinfection; and the control unit is configured to read the temperature as measured by the temperature sensor during disinfection, and to calculate an achieved disinfection dose, and to compare the achieved disinfection dose with the set disinfection dose, and to discontinue an ongoing disinfection if the achieved disinfection dose at least corresponds to the set disinfection dose.

According to yet another aspect of the present invention there is provided an apparatus for thermal disinfection of a fluid path, the apparatus comprising an inlet for receiving a fluid to be used during disinfection of the fluid path, a heating unit connected to the inlet and configured to heat the fluid received from the inlet, an actuator connected to the heating unit and configured to control the flow of the fluid from the heating unit to an outlet, the outlet being configured to connect to the fluid path to be disinfected, a temperature sensor configured to measure the temperature of the fluid in the fluid path, a control unit connected to the actuator and the temperature sensor, the control unit being configured to control the fluid flow by means of the actuator, and to read the temperature measured by the temperature sensor, and that the control unit is configured to receive a set disinfection dose, the control unit is configured to start the disinfection of the fluid path to be disinfected by controlling the actuator to enable fluid from the heating unit to flow to the outlet and further into the fluid path to be disinfected, and the control unit is configured to read the temperature as measured by the temperature sensor during the disinfection, and to calculate the achieved disinfection dose, and to compare the achieved disinfection dose with the set disinfection dose, and to discontinue the disinfection if the achieved disinfection dose at least corresponds to the set disinfection dose.

According to yet another aspect of the present invention a method for performing thermal disinfection of a fluid path is provided, the method comprising the steps of i) receiving at an inlet a fluid to be used during disinfection of the fluid path to be disinfected, ii) heating the fluid received from the inlet, iii) setting a disinfection dose iv) starting the thermal disinfection by controlling an actuator thereby enable heated fluid from the heating unit to flow into the fluid path to be disinfected, v) measuring the temperature of the fluid in the fluid path to be disinfected, vi) calculating an achieved disinfection dose vii) comparing the achieved disinfection dose with the set disinfection dose, and viii) discontinuing the disinfection if the achieved disinfection dose at least corresponds to the set disinfection dose.

An advantage, in respect of at least some embodiments of the present invention, is that energy consumption is lowered compared to conventional disinfection processes, which in turn leads to a disinfection process which puts less load on the environment. Furthermore, the time needed to perform disinfection is reduced which in turn leads to that the available time to treat patients can be increased.

DETAILED DESCRIPTION

Figure 1:
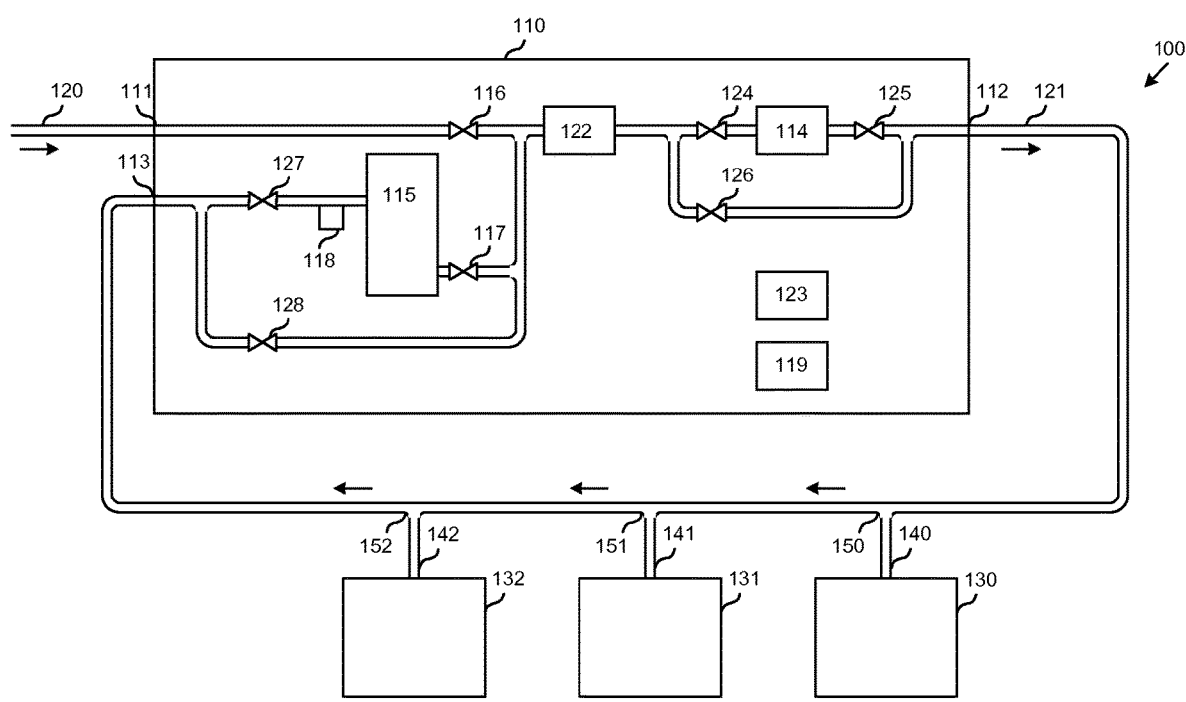
FIG. 1 shows a schematic diagram of a Water System.

FIG. 1 shows a schematic diagram of a Water System 100 of a first embodiment of the invention. The Water System 100 comprises a Water Treatment Unit 110 which is connected to a Water Inlet Pipe 120 at a Treatment Unit Inlet 111. A Pipe Loop Arrangement 121 is connected to a Treatment Unit Outlet 112 and to a Water Return Inlet 113 of the Water Treatment Unit 110. Medical equipments, such as Dialysis Apparatus 130, 131, and 132, are connected to the Pipe Loop Arrangement 121 by means of Dialysis Apparatus Connectors 150, 151, and 152 and Dialysis Apparatus Connecting Pipes 140, 141 and 142. Within the Water Treatment Unit 110 a first side of a First Valve 116 is connected to the Treatment Unit Inlet 111. The second side of the First Valve 116 is connected to an inlet of a Pump 122. The outlet of the Pump 122 is connected to a first side of a Third Valve 124 and a first side of a Fifth Valve 126. The second side of the Third Valve 124 is connected to an inlet of a Water Filter Unit 114. The outlet of the Water Filter Unit 114 is connected to a first side of a Fourth Valve 125. The second side of the Fourth Valve 125 and the Fifth Valve 126 are connected to the Treatment Unit Outlet 112. The Water Return Inlet 113 is connected to a first side of a Sixth Valve 127 and a first side of a Seventh Valve 128. The second side of the Sixth Valve 127 is connected to an input of the Heating Unit 115. The output of the Heating Unit 115 is connected to a first side of the Second Valve 117. The second side of the Second Valve 117 is connected to the second side of the Seventh Valve 128 and the input of the Pump 122. A Temperature Sensor 118 is provided in the vicinity of the Water Return Inlet 113. The Water Treatment Unit 110 also comprises a User Interface 123 for receiving instructions and showing data and messages to a user. The Control Unit 119 is operationally connected to the Temperate Sensor 118, the First, Second, Third, Fourth, Fifth, Sixth and Seventh Valves 116, 117, 124, 125, 126, 127 and 128, the Pump 122, the User Interface 123, the Heating Unit 115, and possibly to other operational components of the Water Treatment Unit 110.

The Water Treatment Unit 110 may be of various sizes spanning from bed-side units (which may be used at a patient's home) to large units providing clean water to portions of or entire clinics or hospitals. A purpose of the Water Treatment Unit 110 is to purify the incoming water. This may be done by the use of reverse osmosis filters (not shown) which may be mounted within a Water Filter Unit 114.

Water purified by the Water Treatment Unit 110, referred to as pure-water, may be used for many purposes. For example, the pure-water may be used during heamodialysis treatment by a dialysis apparatus. The dialysis apparatus prepares dialysis fluid by mixing the pure-water with additional substances and/or dissolve dry compositions. During heamodialysis, the dialysis fluid is made to flow on one side of a semi-permeable membrane (not shown) of a membrane device (such a hollow-fibre membrane) and blood withdrawn from the patient under treatment is made to flow on the other side of the semi-permeable membrane. Haemodialysis is performed by the diffusive transfer across the membrane due to different concentration of substances and/or convective transfer when a trans-membrane pressure is applied across the membrane.

In a first mode of operation, when the Water Treatment Unit 110 provides pure-water at the Treatment Unit Outlet 112, the First, Third, Fourth, and Seventh Valves 116, 124, 125, 128 are opened and the Second, Fifth, Sixth Valves 117, 126, 127 are closed by the Control Unit 119. Water from the Water Inlet Pipe 120 enters the Water Treatment Unit 110 via the Treatment Unit Inlet 111 and is lead through the First Valve 116 and further to the Pump 122 which pumps the water into the Water Filter Unit 114 after having passed the Third Valve 124. The Water Filter Unit 114 purifies the water before it continues through the Fourth Valve 125 and through the Treatment Unit Outlet 112 and into the Pipe Loop Arrangement 121. Apparatus in need of pure-water are connected to the Pipe Loop Arrangement 121. FIG. 1 illustrates three Dialysis Apparatus 130, 131, and 132 (although it could be any number, including a single, of connected equipments) which have been connected by means of the Dialysis Apparatus Connecting Pipes 140, 141 and 142, respectively. The Pipe Loop Arrangement 121 ends after the last connected Dialysis Apparatus (Dialysis Apparatus 132 in FIG. 1) in the Water Return Inlet 113 of the Water Treatment Unit 110. The water returned to the Water Treatment Unit 110 through the Water Return Inlet 113 goes through the Seventh Valve 128 and is lead to the input of the Pump 122 and thereby pumped by the Pump 122 into the Water Filter Unit 114 again. The water returned to the Water Treatment Unit 110 is thereby filtered before being provided anew into the Pipe Loop Arrangement 121.

Advanced Water Treatment Units, using for example reverse osmosis membranes, may remove microbiological contaminants very effectively. In spite of this, bacteria will, over time, proliferate on the surfaces of the pure-water side downstream of the reverse osmosis membranes, causing secondary contamination and biofilm formation in the entire fluid system. In order to prevent or reduce such contamination and film formation preventive disinfection on all parts of the system needs to be performed.

One way of carrying out such preventive disinfection is by thermal disinfection, that is, to let hot water circulate in the fluid system. In a second mode of operation, the Water Treatment Unit 110 provides heated water for thermal disinfection at the Treatment Unit Outlet 112. In this second mode of operation, the Second, Fifth, Sixth Valves 117, 126, 127 are opened and the First, Third Fourth, Seventh Valves 116, 124, 125, 128 are closed by the Control Unit 119. The Control Unit 119 controls the Heating Unit 115 to heat the water. In this particular embodiment, the Heating Unit 115 receives water from the Water Return Inlet 113, that is, water which has passed the Pipe Loop Arrangement 121. In an alternative embodiment (not shown) the water to the Heating Unit 115 may be provided directly from the Water Inlet Pipe 120/Treatment Unit Inlet 111, possibly under the control of an additional valve (not shown). The Heating Unit 115 may also comprise a tank for accumulating (heated or to be heated) water. The heated water is made to flow through the fluid system (including the Pump 122, applicable internal piping arrangements within the Water Treatment Unit 110, the Pipe Loop Arrangement 121, the Dialysis Apparatus Connecting Pipes 140 to 142, and, if the Dialysis Apparatus 130 to 132 allow for disinfection by means of externally provided heated water, the portions of the connected Dialysis Apparatus 130 to 132 to be disinfected). More in detail, the Control Unit 119 controls the Heating Unit 115 to heat the water. The heated water is lead through the Second Valve 117 and further to the Pump 122 which pumps the heated water through the Fifth Valve 126 and to the Treatment Unit Outlet 112 and into the Pipe Loop Arrangement 121. The water of the Pipe Loop Arrangement 121 is returned to the Water Treatment Unit 110 at the Water Return Inlet 113 where it goes through the Sixth Valve 127 and back to the Heating Unit 115. The returned water is heated again and thereafter let out from the Heating Unit 115 and to the Pump 122 anew after having passed the Second Valve 117.

In an alternative mode of operation, the Water Filter Unit 114 may be disinfected by thermal disinfection as well. This is achieved by the Control Unit 119 opening the Third and Fourth Valves 124, 125 and closing the Fifth Valve 126.

The Control Unit 119 is adapted/configured to control the purification and thermal disinfection according to the operations of the embodiments of the present invention. The Control Unit 119 may comprise analogue electronic circuits and/or at least one microprocessor with related data-bus connected to at least one memory device (semiconductor memory, hard-disc drive, USB-memory, etc), communication devices, etc, wherein the memory is provided with software code which adapts/configures the at least one microprocessor to carry out the above mentioned operations.

According to the standard ISO 15883-1:2009 "Washer-disinfectors—Part 1: General requirements, terms and Definition" the definition of cleaning is "removal of contamination from an item to the extent necessary for its further processing and its intended subsequent use". Disinfection is specified by reference to time and temperature for thermal disinfection. According to the standard, whenever practical, thermal disinfection is preferred as it is more easily controlled and avoid the hazards to staff, patients and the environment that can occur through the use of chemical disinfectants.

The definition of the heat disinfection process may be achieved by means of the $A_0$ method which uses knowledge of the lethality of the particular process at different temperatures to assess the overall lethality of the cycle and express this as the equivalent exposure time at a specified temperature. A is defined as the equivalent time in seconds at 80° C. to produce a given disinfection effect. When the z value is 10° C., the term $A_0$ is used. The $A_0$ value of a the heat disinfection process is the equivalent time in seconds at a temperature of 80° C. delivered by that process to the product with reference to micro organisms possessing a z value of 10° C. $A_0$ can be expressed mathematically as is shown in formula 1.

$$A_0 = \Sigma 10^{[(T-80)/z]} \times \Delta t \quad \text{(formula 1)}$$

where $A_0$ is the A value when z is 10° C.; t is the chosen time interval, in seconds; T is the temperature in the load, in degrees Celsius. A lower temperature limit for the integration is set at 65° C.

Figure 6:
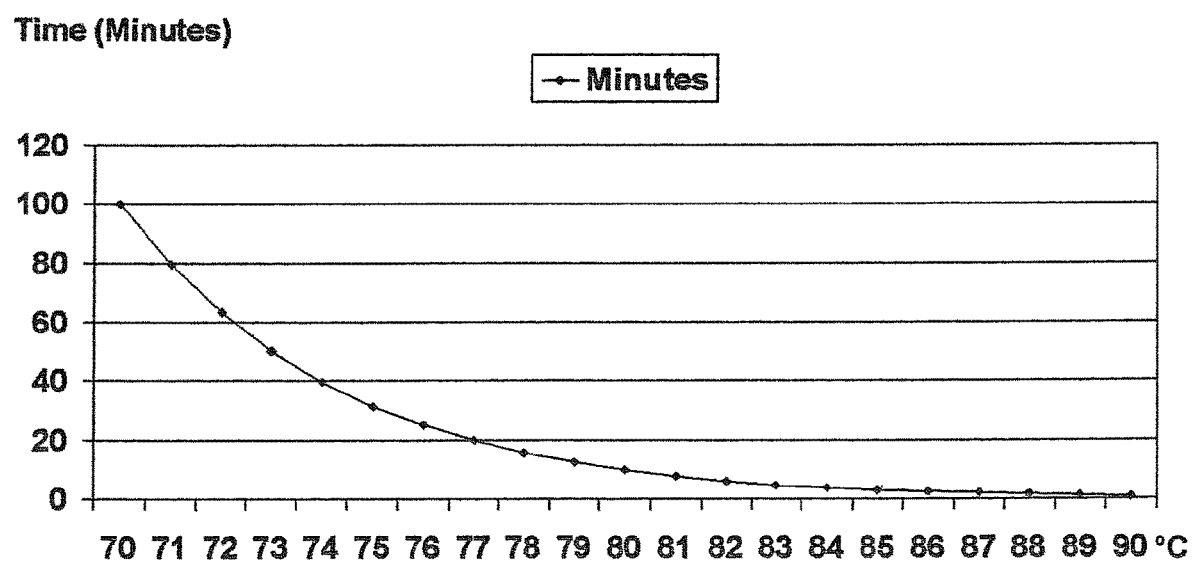
FIG. 6 shows a diagram with the relationship between Time and Temperature for $A_0=600$.

Consequently, $A_0$ is a time related unit which is dependent on temperature. As an example, $A_0$=600 may be achieved by 10 min at 80° C., or by 1 min at 90° C. or by 100 min at 70° C. FIG. 6 shows a diagram with the relationship between Time and Temperature for $A_0$=600.

For reprocessing of medical devices $A_0$=600 to $A_0$=3000 appears to be appropriate.

According to ISO 23500:2011 "Guidance for the preparation and quality management of fluids for haemodialysis and related therapies", guidance is given for water systems to carry out thermal disinfection for at least 10 minutes at 80° C."

The required Disinfection Dose may be pre-calculated or established based on measurements of the contamination (possibly over time) experienced within the fluid system. The required Disinfection Dose would normally be dependent on the actual installation and the number of and/or the thermal disinfection requirements of the connected equipments (e.g. Dialysis Apparatus 130 to 132). Other parameters which may influence the Disinfection Dose are the length of, and diameter, of the pipes of the Pipe Loop Arrangement 121 as well as the flow rates used and the insulations of the piping.

The Control Unit 119 of the Water Treatment Unit 110 may receive information on the required Disinfection Dose (the Disinfection Dose $A_{0\_set}$) through the User Interface 123 as entered by a user, and/or from an external unit (not shown), or it may be fixed during manufacturing or installation. The Disinfection Dose may correspond to a set or calculated $A_0$ value (for example the Disinfection Dose may be set to 600 corresponding to $A_0$=600).

The Water Treatment Unit 110 is provided with the Temperature Sensor 118 which measures the temperature of the water in the fluid system. The Temperature Sensor 118 may be integrated into the Water Treatment Unit 110 or may be located exterior thereto. Preferably, the Temperature Sensor 118 is placed at a location of the fluid system which experiences the lowest, or one of the lowest, temperatures during thermal disinfection or in the proximity thereof. This location would normally be at the end of the fluid loop such as either in the vicinity before or after the Water Return Inlet 113.

Figure 2:
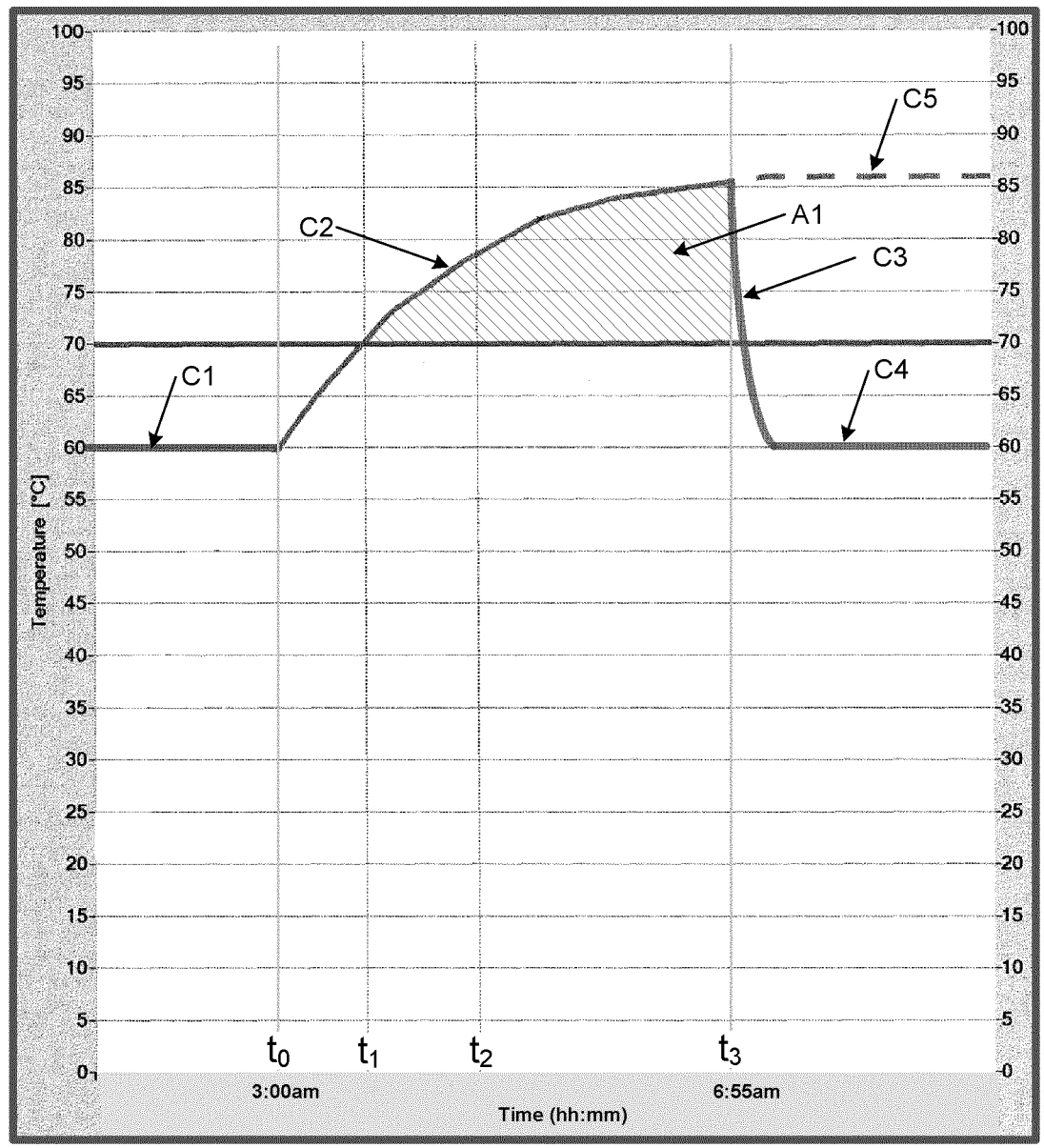
FIG. 2 illustrates an example of how the temperature may vary as a function of time during a disinfection process.

FIG. 2 illustrates an example of how the temperature may vary as a function of time during a disinfection process according to an embodiment of the invention. The y-axis represents the temperature as measured by the Temperature Sensor 118. At time $t_0$, in this example at 3:00 am, the Control Unit 119 is given a command to initiate thermal disinfection. The command may be entered by a user (e.g. through the use of the User Interface 123), and/or received from another unit (not shown), and/or as triggered by a timer and/or at a set time (possibly realized by a function of the Control Unit 119 together with the User Interface 123), etc. When the Control Unit 119 has identified the initiation of the thermal disinfection, the Control Unit 119 enables hot water to circulate in the fluid system. This is done for example according to the second mode of operation of the Water Treatment Unit 110 as explained above. In the particular example of FIG. 2, the Control Unit 119 has controlled the Heating Unit 115 such that water stored in the Heating Unit 115 has been warmed up and maintained, prior to the initiation of the disinfection process, at a set temperature which, in the example shown in FIG. 2 is set at 60° C. as indicated by the curve C1. The curve C2 shows that the measured temperature is building up from the set temperature of 60° C. The Control Unit 119 either waits a predefined time enabling the heated water to reach the end of the Pipe Loop Arrangement 121 (close to the Water Return Inlet 113) or it measures the temperature by means of the Temperature Sensor 118 and waits until it reaches a defined threshold (for example a temperature above 65° C.). In the example of FIG. 2 the threshold temperature has been set to 70° C. and as is shown in FIG. 2 this temperature is achieved at time $t_1$. From this point of time and onwards during the disinfection process, the Control Unit 119 measures the temperature by means of the Temperature Sensor 118 (which is assumed to be the lowest (or one of the lowest) temperature in the fluid system) and calculates (continuously, regularly, and/or occasionally) the achieved Disinfection Dose $A_{0\_achieved}$ based on formula 1 with a known or given value of z. The Control Unit 119 compares the calculated achieved Disinfection Dose $A_{0\_achieved}$ with a set Disinfection Dose $A_{0\_set}$. Times $t_2$ and $t_3$ in FIG. 2 illustrate times when such calculations and comparisons have been carried out. If, such as at time $t_2$, the achieved Disinfection Dose $A_{0\_achieved}$ does not equal or exceed the set Disinfection Dose $A_{0\_set}$ then the Control Unit 119 continues the disinfection process. If the achieved Disinfection Dose $A_{0\_achieved}$ equals or exceeds the set Disinfection Dose $A_{0\_set}$ then the Control Unit 119 discontinuous the disinfection process, which is the case at time $t_3$ (symbolically the contribution to the achieved Disinfection Dose $A_{0\_achieved}$ at time $t_3$ has been illustrated by the dashed lines labelled A1). The disinfection process is discontinued by closing the Second Valve 117 and thereby no longer letting the heated water out from the Heating Unit 115. As is illustrated by curve C3 of FIG. 2, at the time the heated water is no longer let out from the Heating Unit 115, the temperature of the water in the system, as measured by the Temperature Sensor 118, drops. The Control Unit 119 may control the Heating Unit 115 to maintain the water stored in the Heating Unit 115 at a set temperature, which, in the example shown in FIG. 2 is set at 60° C. as indicated by the curve C4. The Control Unit 119 may also open the First Valve 116, thereby allowing cooler water to be circulated in the water system (which may lead to a quicker decrease of the temperature compared to what is illustrated by curve C3).

The dotted curve, curve C5, illustrates the temperature of the water in the system if the Control Unit 119 had not discontinued the disinfection process at the time the set Disinfection Dose had been achieved (at time $t_3$). Consequently, the present invention prevents the unnecessary waste of energy (by warming up and circulating hot water) which would have occurred if the process had not been discontinued; unnecessary waste of energy since the circulation of warm water during this period of time (that is, after time $t_3$) is not required from a disinfection point of view. Such waste of energy may be huge for example if the disinfection process were to run a full night. The present invention also finalizes the disinfection process quicker and thereby shortens the time during which patients cannot be treated due to the occurrence of the disinfection process. It should be noted that the disinfection provided by the heated water (above the threshold temperature of 70° C. in the example of FIG. 2) while the temperature thereof is building up (see curve C2) is also taken into account of by the present invention when calculating the achieved Disinfection Dose which, compared to a system where the temperature has to reach a very high temperature (e.g. 90° C.) before thermal disinfection is initiated, thereby shortens the time required for the thermal disinfection.

The structure of the water system and number of and structure of the connected medical equipment do normally not change significantly over time. Consequently, the water system may use historic information to estimate the completion time of the disinfection process. For example, for a set Disinfection Dose, the duration of the previous disinfection process would normally match the time required for the next disinfection process quite well.

Figure 3:
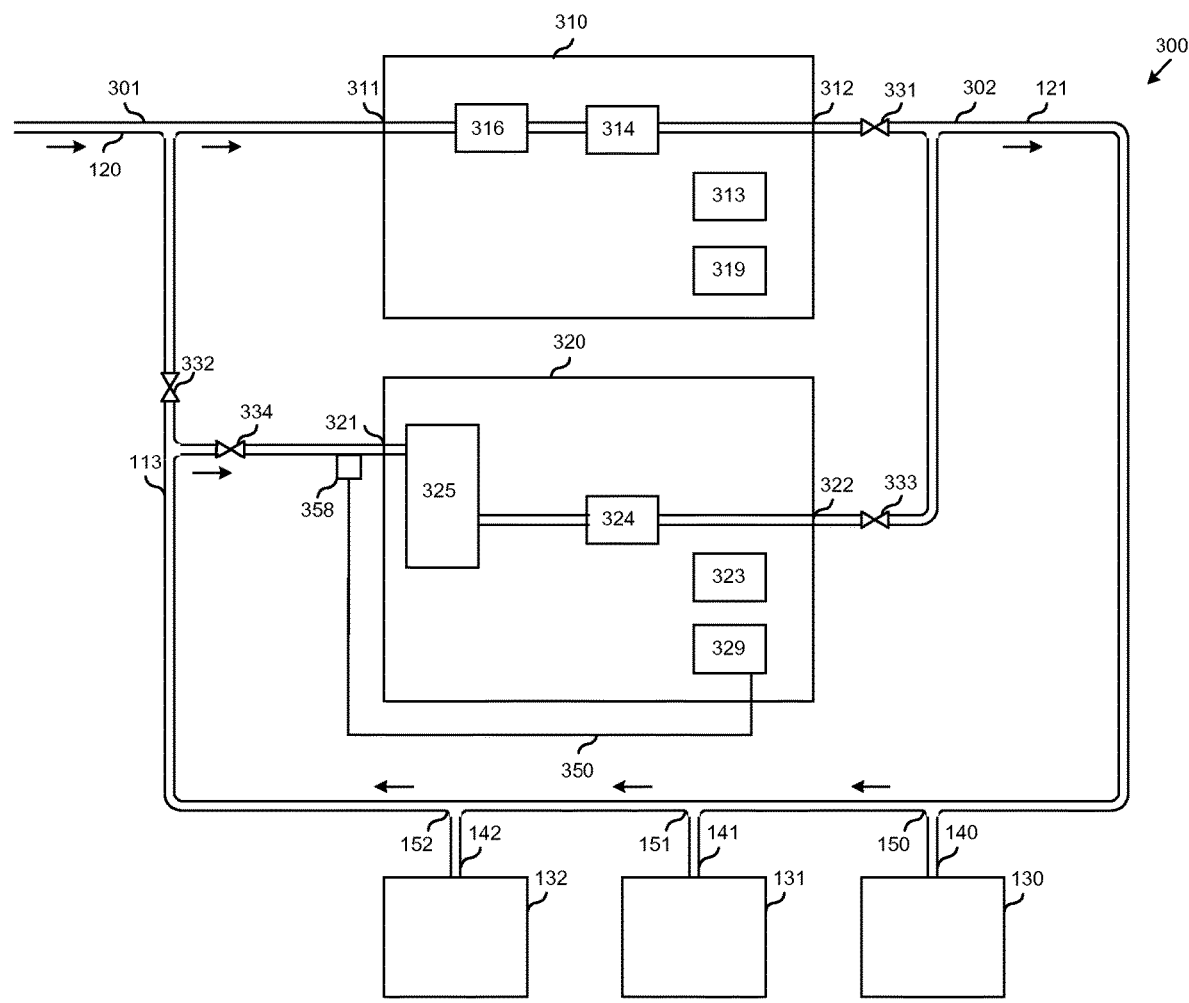
FIG. 3 shows a schematic diagram of a Distributed Water System

FIG. 3 shows a schematic diagram of a Distributed Water System 300 of an alternative embodiment of the present invention. The components in FIG. 3 having similar functions to the components of the embodiments discussed in conjunction with FIG. 1 have been given the same reference numbers. In this embodiment of the invention, which may be combined with other embodiments of the present invention, thermal disinfection and the control thereof is provided by a separate Water Heating Unit 320. In this case, the purification of the water may be provided by a Distributed Water Treatment Unit 310.

The Water Inlet Pipe 120 is connected via a DWS Inlet 301 to the Distributed Water Treatment Unit 310 at a DWTU Inlet 311. The DWTU Inlet 311 is connected to an inlet of a DWTU Pump 316. The outlet of the DWTU Pump 316 is connected to an inlet of a DWTU Filter Unit 314. The outlet of the DWTU Filter Unit 314 is connected to a DWTU Outlet 312. The Distributed Water Treatment Unit 310 is provided with a DWTU Control Unit 319 and a DWTU User Interface 313. The DWTU Control Unit 319 is operationally connected to components of the Distributed Water Treatment Unit 310, such as for example the DWTU Pump 316 and the DWTU User Interface 313.

The WHU Inlet 321 is connected to an inlet of a WHU Heating Unit 325. The outlet of the WHU Heating Unit 325 is connected to an inlet of a WHU Pump 324. The outlet of the WHU Pump 324 is connected to an WHU Outlet 322. The Water Heating Unit 320 is provided with a WHU Control Unit 329 and a WHU User Interface 323. The WHU Control Unit 329 is operationally connected to and controls components of the Water Heating Unit 320, such as for example the WHU Heating Unit 325, the WHU Pump 324 and the WHU User Interface 323.

The Distributed Water System 300 further comprises a DWS First Valve 331 which is connected to the DWTU Outlet 312 on one side and a DWS Outlet 302 on the other side. Similarly, the system comprises a DWS Third Valve 333 which is connected to the WHU Outlet 322 on one side and the DWS Outlet 302 on the other side. The DWS Outlet 302 is connected to the Pipe Loop Arrangement 121. The end of the Pipe Loop Arrangement is connected via Water Return Inlet 113 to first sides of a DWS Second and DWS Fourth Valves 332, 334. The second side of the DWS Second Valve 332 is connected to the Water Inlet Pipe 120 and the second side of the DWS Fourth Valve 334 is connected to the WWU Inlet 321. A DWS Temperature Sensor 358 is located at the vicinity of the WHU Inlet 321. The DWS Temperature Sensor 358 is operationally connected to the WHU Control Unit 329 by means of a Cable 350.

The DWS Inlet 301, DWS Outlet 302 and the Water Return Inlet 113 may be physical connection devices and/or may only represent physical locations in the water system (without constituting physical devices per se).

In one alternative embodiment, the DWS First, DWS Second, DWS Third, and DWS Fourth Valves 331, 332, 333, 334 are operationally connected to and controlled by the WHU Control Unit 329.

In a first mode operational of the Distributed Water System, the Distributed Water Treatment Unit 310 provides pure-water at the DWTU Outlet 312. The DWS First, and DWS Second Valves 331 and 332 are opened and the DWS Third and DWS Fourth Valves 333, 334 are closed by the Control Unit 329. Water from the Water Inlet Pipe 120 enters the Distributed Water Treatment Unit 310 via the DWTU Inlet 311 and is lead to the DWTU Pump 316 which pumps the water into the DWTU Filter Unit 314. The DWTU Filter Unit 314 purifies the water before it continues to the DWTU Outlet 312 and into the Pipe Loop Arrangement 121 after having passed the DWS First Valve 331. Similar to above, pure-water is provided to Apparatus in need of pure-water which are connected to the Pipe Loop Arrangement 121. At the end of the Pipe Loop Arrangement 121 the water is returned to the DWTU Inlet 311 after having passed the DWS Second Valve 332. The water returned to the Distributed Water Treatment Unit 310 is thereby filtered before being provided anew into the Pipe Loop Arrangement 121.

In a second mode of operation of the Distributed Water System, the Water Heating Unit 320 provides heated water for thermal disinfection at the WHU Outlet 322. In this second mode of operation, the DWS Third and DWS Fourth Valves 333, 334 are opened and the DWS First and DWS Second Valves 331, 332 are closed by the WHU Control Unit 329. The WHU Control Unit 329 controls the WHU Heating Unit 325 to heat the water. The WHU Heating Unit 325 may also comprise a tank for accumulating (heated or to be heated) water. The heated water is made to flow through the fluid system (including the WHU Pump 324, applicable internal piping arrangements within the Water Heating Unit 320, the Pipe Loop Arrangement 121, the Dialysis Apparatus Connecting Pipes 140 to 142, and, if the Dialysis Apparatus 130 to 132 allow for disinfection by means of externally provided heated water, the portions of the connected Dialysis Apparatus 130 to 132 to be disinfected). More in detail, the WHU Control Unit 329 controls the WHU Heating Unit 325 to heat the water. The heated water is lead to the WHU Pump 324 which pumps the heated water through the WHU Outlet 322, through the DWS Third Valve 333 and into the Pipe Loop Arrangement 121. The water of the Pipe Loop Arrangement 121 is returned to the WHU Heating Unit 325 by going through the DWS Fourth Valve 334 and the WHU Inlet 321.

In this particular embodiment, the WHU Heating Unit 325 receives water from the Water Return Inlet 113 (when the DWS Fourth Valve is open), that is, water which has passed the Pipe Loop Arrangement 121. In an alternative embodiment (not shown) the water to the WHU Heating Unit 325 may be provided directly from the Water Inlet Pipe 120/ DWS Inlet 301, possibly under the control of an additional valve (not shown).

In an alternative embodiment, which may be combined with other embodiments of the present invention, the DWS First, DWS Second, DWS Third, and DWS Fourth Valves 331, 332, 333, 334 may be located within the Water Heating Unit 320 or the Distributed Water Treatment Unit 310 in any possible combination. Additionally, the DWS Temperature Sensor 358 may be located within the Water Heating Unit 320. Furthermore, the control of the Distributed Water System may be exercised by the DWTU Control Unit 319 or the WHU Control Unit 329 or a combination thereof. Of course, the operational components to be controlled by a control unit have to be connected in some manner to that control unit in order to enable such control.

In an alternative embodiment, which may be combined with other embodiments of the present invention, the Distributed Water Treatment Unit 310 may be provided with its own heating unit (not shown) for enabling thermal disinfection of the DWTU Filter Unit 314 and internal piping arrangements and other components.

In a further alternative embodiment, which may be combined with other embodiments of the present invention, the Pipe Loop Arrangement 121 does not lead the water back to the Water Treatment Unit 110. Instead, the end of the Pipe Loop Arrangement 121 is connected to a drain (not shown).

In a further embodiment of the present invention medical equipment with ability to perform thermal disinfection is provided. The medical equipment may or may not have its own heating unit to generate the hot water for the disinfection process. Such medical equipment (e.g. Dialysis Apparatus) may be one kind of equipment which could be connected as connected equipment of the embodiments of the present invention discussed above. It may, however, not be necessary to include the heating unit within the medical equipment if the equipment is provided with heated water for thermal disinfection from the Water System 100.

Figure 4:
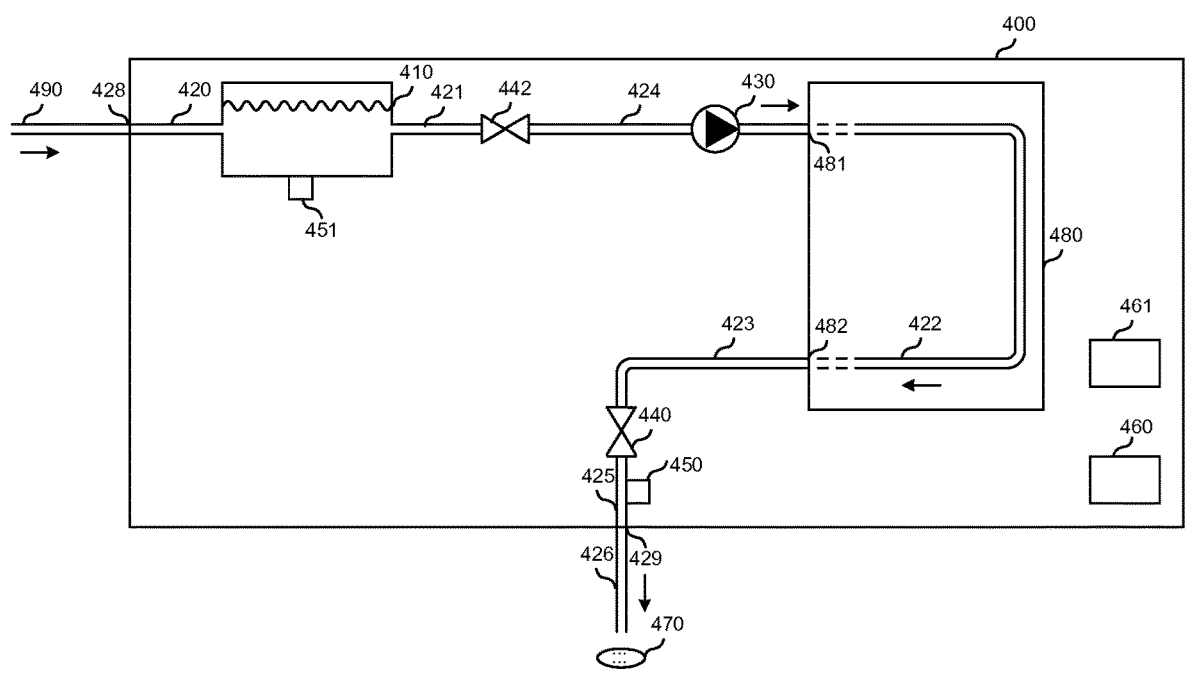
FIG. 4 shows a schematic diagram of medical equipment.

FIG. 4 shows a schematic diagram of medical equipment which in this embodiment is a Dialysis Apparatus 400. Water is provided to the Dialysis Apparatus 400 by means of a Connection Tube 490 which connects to a DA Inlet 428 of the Dialysis Apparatus 400. The Dialysis Apparatus 400 comprises a DA Heating Unit 410 which is connected by an Inlet Tube 420 to the DA Inlet 428. The outlet of the DA Heating Unit 410 is connected by a First Tube 421 to an inlet of a Water Inlet Valve 442. The outlet of the Water Inlet Valve 442 is connected by a Fourth Tube 424 to the inlet of a DA Pump 430. The Dialysis Apparatus comprises a number of tubes and components which need to be disinfected during a thermal disinfection process. These tubes and components have been illustrated by the box DA Components 480 (further illustrated by the dotted tube lines and the Second Tube 422). The outlet of the DA Pump 430 is connected by means of the DA Components Inlet Connector 481 to the DA Components 480 and the outlet therefrom is connected, by means of the DA Components Outlet Connector 482 and a Third Pipe 423 to an inlet of a Water Dispose Valve 440. The outlet of the Water Dispose Valve 440 is connected by means of a Fifth Tube 425 to a DA Outlet 429, and a Drain Tube 426, connected to the DA Outlet 429, leads fluid therein to a Drain 470. A First Temperature Sensor 450 is located in the vicinity of the DA Outlet 429 such that it can sense the temperature of the water within the Fifth Tube 425 (with certain accuracy). This location would normally constitute the lowest, or one of the lowest, temperatures of the fluid path. In an alternative embodiment (not shown) the First Temperature Sensor is placed in an alternative location on the fluid path and its measure could be used (e.g. if it is assumed that the temperature at that location substantially corresponds to the temperature of the lowest temperature or as a representation of the lowest temperature of the fluid path with or without a correction (for example by the subtraction of a fixed term or by means of a correction formula)). A Second Temperature Sensor 451 is located at the DA Heating Unit 410 such that it can sense the temperature of the water within the DA Heating Unit 410 (with certain accuracy). The Dialysis Apparatus further comprises a DA Control Unit 460 which is adapted/configured to control the operations of at least the thermal disinfection process of the Dialysis Apparatus 400 and a DA User Interface 461 for receiving instructions and showing data and messages to a user. In this embodiment, the DA Control Unit 460 is operationally connected to the DA User Interface 461, the Water Dispose Valve 440, the Water Inlet Valve 442, the DA Heating Unit 410, the First Temperature Sensor 450, the Second Temperature Sensor 451, and the DA Pump 430 (and may be connected to any other operational component of the Dialysis Apparatus). The DA Control Unit 460 is adapted/configured to control the thermal disinfection according to the operations of the embodiments of the present invention. The DA Control Unit 460 may comprise analogue electronic circuits and/or at least one microprocessor with related data-bus connected to at least one memory device (semiconductor memory, hard-disc drive, USB-memory, etc), communication devices, etc, wherein the memory is provided with software code which adapts/configures the at least one microprocessor to carry out the above mentioned operations.

In an alternative embodiment, which may be combined with other embodiments of the present invention, the medical equipment, such as Dialysis Apparatus 400, may be equipped with components (tubes, valves, etc) such that the disinfection path becomes a circuit in which heated water may circulate during thermal disinfection. For example, the control unit may control one or several valves in order to establish such a circuit during thermal disinfection. With reference to FIG. 4, such a circuit may be established if an additional valve is connected between the Third Tube 423 and Fourth Tube 424. In this case, the First Temperature Sensor 450 would normally be located at the end of the so created circuit (in order to sense the lowest, or one of the lowest, temperature of the circuit), which is on the downstream side of the additional valve.

Figure 5:
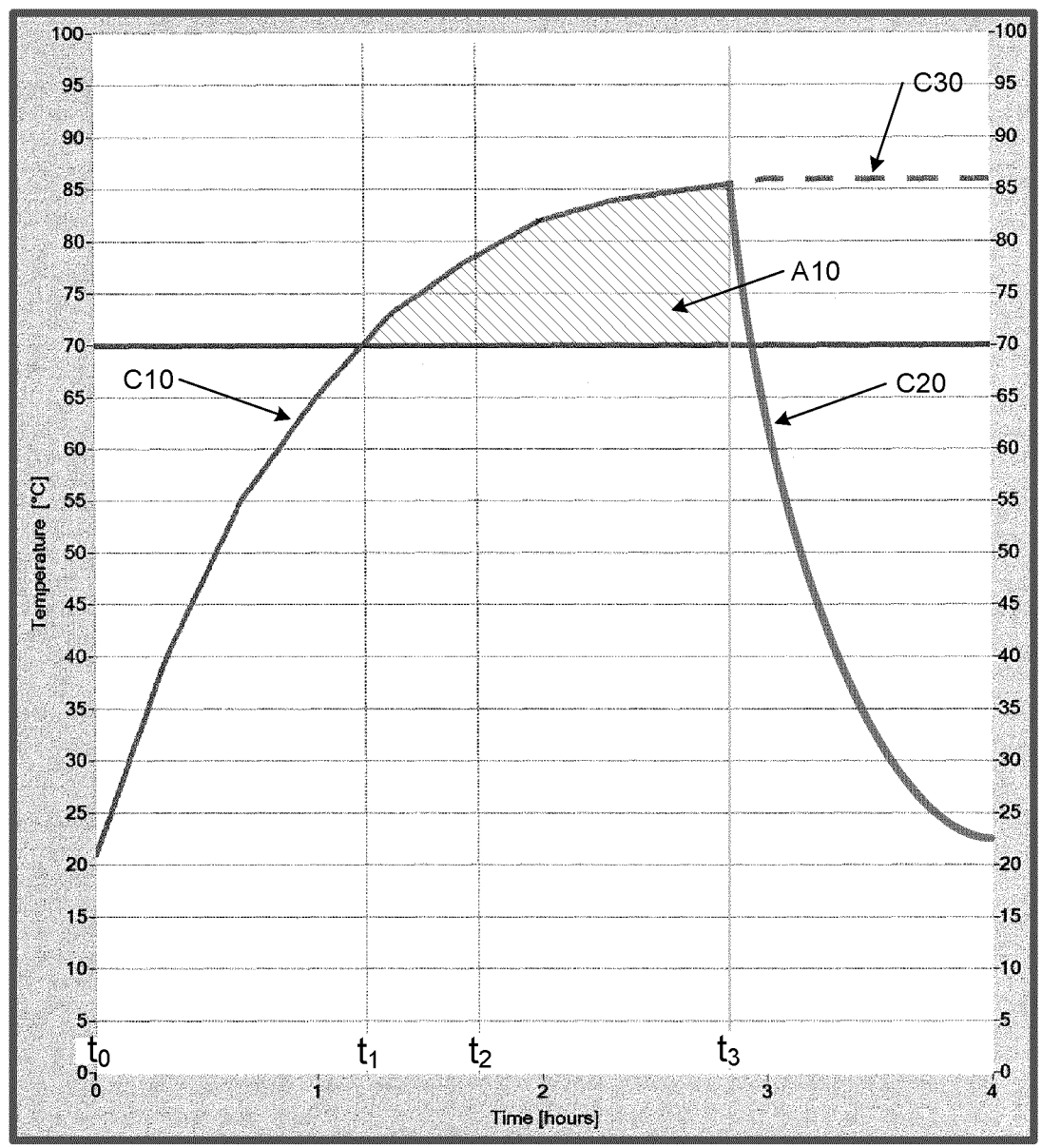
FIG. 5 illustrates another example of how the temperature may vary as a function of time during a disinfection process.

FIG. 5 illustrates another example of how the temperature may vary as a function of time during a disinfection process according to an embodiment of the invention. The y-axis represents the temperature as measured by the First Temperature Sensor 450. At time zero $t_0$ the DA Control Unit 460 is given a command to initiate thermal disinfection. The command may be entered by a user (e.g. through the use of the DA User Interface 461), and/or received from another unit (not shown), and/or as triggered by a timer and/or at a set time (possibly realized by a function of the DA Control Unit 460 together with the DA User Interface 461), etc. When the DA Control Unit 460 has identified the initiation of the thermal disinfection, the DA Control Unit 460 instructs the DA Heating Unit 410 (which may also accumulate heated water) to heat the water. The DA Control Unit 460 also enables the heated water to flow in the fluid system, which is done by opening the Water Inlet Valve 442 and starting the DA Pump 430, and thereby letting heated water out through the Water Inlet Valve 442 and further by means of the DA Pump 430 into the DA Components 480. In this particular example, the temperature of the water is initially approximately 21° C. Consequently, as is shown by the curve C10 the measured temperature is building up from initial approximately 21° C. The DA Control Unit 460 either waits a predefined time enabling the heated water to reach the end of the fluid path, that is, in the vicinity of the DA Outlet 429 or it measures the temperature by means of the First Temperature Sensor 450 and waits until it reaches a defined threshold (for example a temperature above 65° C.). In the example of FIG. 5 the threshold temperature has been set to 70° C. and as is shown in FIG. 5 this temperature is achieved at time $t_1$. From this point of time and onwards during the disinfection process, the DA Control Unit 460 measures the temperature by means of the First Temperature Sensor 450 (which is assumed to be the lowest (or one of the lowest) temperature in the fluid system) and calculates (continuously, regularly, and/or occasionally) the achieved Disinfection Dose $A_{0\_achieved}$ based on formula 1 with a known or given value of z. The DA Control Unit 460 compares the calculated achieved Disinfection Dose $A_{0\_achieved}$ with a set Disinfection Dose $A_{0\_set}$. Times $t_2$ and $t_3$ in FIG. 5 illustrate times when such calculations and comparisons have been carried out. If, such as at time $t_2$, the achieved Disinfection Dose $A_{0\_achieved}$ does not equal or exceed the set Disinfection Dose $A_{0\_set}$ then the DA Control Unit 460 continues the disinfection process. If the achieved Disinfection Dose $A_{0\_achieved}$ equals or exceeds the set Disinfection Dose $A_{0\_set}$ then the DA Control Unit 460 discontinuous the disinfection process, which is the case at time $t_3$ (symbolically the contribution to the achieved Disinfection Dose $A_{0\_achieved}$ at time $t_3$ has been illustrated by the dashed lines labelled A10). The disinfection process is discontinued by the DA Control Unit 460 instructing the DA Heating Unit 410 to stop warming the incoming water and/or closing the Water Inlet Valve 442. At this point of time the DA Control Unit 460 may empty the fluid path by closing the Water Inlet Valve 442 (if not already done) and opening the Water Dispose Valve 440, whereby the water in the fluid path will be pumped by the DA Pump 430 to the Drain 470. As is illustrated by curve C20 of FIG. 5, at the time water is no longer heated by the DA Heating Unit 410, the temperature of the water in the system, as measured by the First Temperature Sensor 450, drops.

The dotted curve, curve C30, illustrates the temperature of the water in the system if the DA Control Unit 460 had not discontinued the disinfection process at the time the set Disinfection Dose had been achieved (at time $t_3$). Consequently, the present invention prevents the unnecessary waste of energy (by warming up and circulating hot water) which would have occurred if the process had not been discontinued; unnecessary waste of energy since the circulation of warm water during this period of time (after time $t_3$) is not required from a disinfection point of view. Such waste of energy may be huge for example if the disinfection process were to run a full night. The present invention also finalizes the disinfection process quicker and thereby shortens the time during which patients cannot be treated due to the occurrence of the disinfection process. It should be noted that the disinfection provided by the heated water (above the threshold temperature of 70° C. in the example of FIG. 5) while the temperature thereof is building up (see curve C10 after the time $t_1$) is also taken into account of by the present invention when calculating the achieved Disinfection Dose which, compared to a system where the temperature has to reach a very high temperature (e.g. 90° C.) before thermal disinfection is initiated, thereby shortens the time required for the thermal disinfection.

In an alternative embodiment of medical equipment, the medical equipment receives the hot water to be used for thermal disinfection from another unit (for example from a Water System as disclosed above) and thereby does not need to have the capability to heat the fluid during disinfection itself. Such an alternative embodiment would be a Dialysis Apparatus as shown in FIG. 4 but without the DA Heating Unit 410. The hot water for thermal disinfection is then provided to the Dialysis Apparatus by means of a Connection Tube 490. The Connection Tube 490 connects to a DA Inlet 428 of the Dialysis Apparatus 400. In this embodiment, the First Tube 421 directly connects the DA Inlet 428 to the inlet of a Water Inlet Valve 442.

The operation of the embodiment discussed above in relation to FIG. 5 (where a DA Heating Unit 410 is present) would be similar for this embodiment. The difference is that, when the DA Control Unit 460 has identified the initiation of the thermal disinfection, the DA Control Unit 460 enables the heated water to flow in the fluid system, which is done by opening the Water Inlet Valve 442 and starting the DA Pump 430, and thereby letting heated water received through the DA Inlet 428 (and further through the First Tube 421) out through the Water Inlet Valve 442 and further by means of the DA Pump 430 into the DA Components 480. A further difference is that when the disinfection process is discontinued by the DA Control Unit 460 the DA Control Unit 460 closes the Water Inlet Valve 442. For this embodiment, the DA Control Unit 460 will differ to its configuration from the previous embodiment to the extent the operations differs.

The structure of the medical equipment does normally not change over time. Consequently, the medical equipment may use historic information to estimate the completion time of the disinfection process. For example, for a set Disinfection Dose, the duration of the previous disinfection process would normally match the time required for the next disinfection process quite well.

In alternative embodiments of the Water System and Dialysis Apparatus, which may be combined with other embodiments of the present invention, the Control Unit 119, WHU Control Unit 329, DA Control Unit 460 (reference to any one is henceforth referred to as the CU) stores the achieved Disinfection Dose $A_{0\_achieved}$ as a function of time in its memory (not shown). For example, the CU may store in its memory the times required to achieve Disinfection Doses of 1000, 2000, 3000, etc. The stored values for each Disinfection Dose may be dependent only on measurements at the time the previous disinfection was performed or may be calculated representative values such as average values or max values from at least two previous disinfections. The CU then, during the following (on-going) disinfection process, calculates an estimate of the remaining time, and/or a completion time, for the on-going disinfection process based on the progress of the on-going disinfection process measured in achieved Disinfection Dose $A_{0\_achieved}$ and the stored information on the time required to achieve the remaining Disinfection Dose (to reach the set Disinfection Dose $A_{0\_set}$). The CU may interpolate and/or extrapolate the time required to achieve the remaining Disinfection Dose based on the stored information (e.g. if the corresponding Disinfection Dose is not immediately available from the information stored in the memory). For example, if the CU has stored times corresponding to Disinfection Doses of 1000, 2000, 3000, etc, the set Disinfection Dose is set to 3000 and the remaining Disinfection Dose has been calculated to be 500 then the CU may calculate the remaining time as the time for achieving the Disinfection Dose of 3000 (as retrieved from the memory) minus the time for achieving the Disinfection Dose of 2500 where the latter value is calculated by the interpolation of the times corresponding to the Disinfection Doses 2000 (as retrieved from the memory) and 3000 (as retrieved from the memory) at 2500. In a further alternative embodiment, the CU receives information, for example from a user by means of the User Interface 123/WHU User Interface 323/DA User Interface 461, representing the time to completion (or the actual time of the completion) of the disinfection process. The CU then calculates, based on the stored information (that is, information of the achieved Disinfection Dose $A_{0\_achieved}$ as a function of time stored in its memory from at least one disinfection process of the past) for the set Disinfection Dose $A_{0\_set}$, the time when the disinfection process needs to be started (the staring time) in order to be completed at the so set completion time. The CU waits for the calculated starting time and initiates the disinfection process (as is set out above) at that time. For example, if the CU has stored from a previous disinfection process that a set Disinfection Dose of $A_{0\_set}=6000$ normally would take 2 hours and 55 minutes and the user has entered information through the User Interface 123/WHU User Interface 323/DA User Interface 461 that the disinfection process should be ready by 5:55 am (e.g. at the time the morning shift starts to work at the clinic) then the CU calculates that it has to initiate the disinfection process at 3:00 am. The advantage of this embodiment is that the disinfection is carried out as close in time to the use of the water system for treatments as possible thereby reducing the risks of contamination and bacterial growth after the completion of the disinfection process. In an alternative embodiment the CU adds a safety margin of a certain period of time or a certain amount of Disinfection Dose.

The various parameters may be stored in any kind of memory (not shown), including registers, of the CU. The set Disinfection Dose $A_{0\_set}$ may be set by the system and/or received from another unit (not shown) and/or it may be entered by the user e.g. through the User Interface 123/ WHU User Interface/DA User Interface 461 prior to or during an on-going disinfection process.

In alternative embodiments of the Water System and Dialysis Apparatus, which may be combined with other embodiments of the present invention, the calculations by the CU are not carried out by using formula 1 with a known or given value of z but rather through a look-up table or simplified formula giving an approximation corresponding to the relationship provided by formula 1 for a given value of z.

In alternative embodiments of the Water System and Dialysis Apparatus, which may be combined with other embodiments of the present invention, the CU checks at certain intervals that the temperature as measured by the Temperature Sensor 118/DWS Temperature Sensor 358/ First Temperature Sensor 450 does not fall below a defined value (e.g. the defined threshold referred to above). In such a case, the thermal disinfection process may be interrupted and an alarm may be set and displayed on the User Interface 123/WHU User Interface 323/DA User Interface 461 and/or such periods when the temperature falls below the defined value (defined threshold) are discarded when the CU calculates the achieved Disinfection Dose $A_{0\_achieved}$.

In alternative embodiments of the Water System and Dialysis Apparatus, which may be combined with other embodiments of the present invention, the CU continuously, regularly, or occasionally, calculates the disinfection dose achieved so far during the disinfection process and displays this value on the User Interface 123/WHU User Interface 323/DA User Interface 461. The calculation may be achieved in the same manner as discussed above. The disinfection dose achieved may be displayed after the disinfection process has been initiated or at the command at the User Interface 123/WHU User Interface 323/DA User Interface 461 by an operator.

In further embodiments of the Water System and Dialysis Apparatus, which may be combined with any of the other embodiments of the present invention, the calculation of the Disinfection Dose applied by the CU may be made dependent on the frequency of the performed disinfections over a period of the past and/or the time that has lapsed since disinfection was performed last time. For example, if the set Disinfection Dose $A_{0\_set}$ is set such that it comprises a safety margin (e.g. a safety factor) then the frequency and/or period referred to above may be used to influence the size of the safety margin. For example, if the safety margin is set as a factor 10 and the time since last disinfection is determined to be less than 24 h then the dose may be recalculated by the CU such that the safety margin is lowered with a certain amount (e.g. by 50%).

The example of thermal disinfection discussed in conjunction with FIG. 2 may also be implemented in a Dialysis Apparatus by adapting the DA Control Unit 460 accordingly. Furthermore, the example of thermal disinfection discussed in conjunction with FIG. 5 may also be implemented in a Water System by adapting the Control Unit 119 accordingly.

In an alternative embodiment, which may be combined with any other embodiment of the present invention, the Control Unit 119, WHU Control Unit 329, DA Control Unit 460 controls the Heating Unit 115, WHU Heating Unit 325, DA Heating Unit 410, such that the temperature of the water is warmed up to a higher temperature, such as 90° C. or even higher, prior to the initiation of the disinfection process. In this case, the threshold temperature (set to 70° C. in FIG. 2 and FIG. 4) may be achieved in very short time, that is the time between $t_0$ and $t_1$ can be significantly shortened.

The Dialysis Apparatus 130, 131, and 132 of the embodiments discussed in conjunction with FIG. 1 and FIG. 3 could be any type of Dialysis Apparatus including, but not limited to, the Dialysis Apparatus adapted to carry out the thermal disinfection as disclosed above in conjunction with FIG. 4.

In the embodiments relating to FIG. 1 and FIG. 3 above, the Pump 122, the WHU Pump 324, the Second valve 117, and the DWS Third Valve 333 are performing the role of an actuator configured to control the flow of the heated water from the Heating Unit 115/WHU Heating Unit 325 to the Treatment Unit Outlet 112 and WHU Outlet 322, respectively. In the embodiments relating to FIG. 4 above, the Water Inlet Valve 442 and the DA Pump 430 are performing the role of an actuator configured to control the flow of the fluid from the DA Inlet 428 or DA Heating Unit 410 to DA Components Inlet Connector 481 (the fluid path with a need for regular disinfection). The actuator(s) may be realized by means of a single device or (as in the embodiments above) a combination of devices (such as valves, pumps, etc).

It should be noted that for the embodiments discussed in relation to FIG. 1 and FIG. 3 thermal disinfection will be carried out not only on the Pipe Loop Arrangement 121 but also on exposed internal pipes, actuators, devices, filters, components, etc. within the Water Treatment Unit 110 and the Water Heating Unit 320, respectively, from (and including) the Heating Unit 115, WHU Heating Unit 325 all the way to the drain (if any). Dialysis Apparatus Connecting Pipes 140, 141 and 142 and Dialysis Apparatus Connectors 150, 151, and 152 will also be disinfected if the connected medical devices have the capability of letting heated water through.

Similarly, it should be noted that for the embodiments discussed in relation to FIG. 4 thermal disinfection will be carried out not only on the DA Components 480 but also on all internal pipes, actuators, devices, filters, components, etc. within the Dialysis Apparatus 400, from (and including) the DA Inlet 428, or DA Heating Unit 410 (if any) and to the drain (if any).

A fluid path with a need for regular disinfection in this disclosure and claims refers to a fluid path which needs regular or reoccurring disinfection and which may be triggered by for example time events, treatment events, etc.

It should be noted that for the sake of simplicity generally known parts and operations of a Water Systems, Water Treatment Units, and Dialysis Apparatus have not been included in the embodiments above.

Further embodiments of the present inventions are disclosed by the following clauses:

Clause 1. A Water System for providing water to at least one connected device through a fluid path and being able to disinfect the fluid path by means of thermal disinfection, the Water System comprising:
an inlet (111, 301) for receiving water to the Water System;
a heating unit (115, 325) configured to heat water within the Water System;
a filter unit (122, 314) configured to filter water within the Water System in order to provide filtered water to an outlet (112, 302);
an actuator (117, 122, 324, 333) configured to control the flow of water from the heating unit to the outlet;
a fluid path (121) connected to the outlet, the fluid path comprising at least one connector (150, 151, 152) configured to connect to at least one device to which water is provided by the Water System;
a temperature sensor (118, 358) located at the fluid path and configured to measure the temperature of the fluid in the fluid path;
a control unit (119, 329) connected to the heating unit, the actuator and the temperature sensor, the control unit being configured to control the flow of water by means of the actuator, to control the heating of water by the heating unit, and to read the temperature as measured by the temperature sensor;
characterized in that
the control unit is configured to start the disinfection of the fluid path by controlling the heating unit to heat water and controlling the actuator to enable heated water to flow to the outlet and further into the fluid path; and
the control unit is configured to read the temperature as measured by the temperature sensor during the disinfection, and to calculate an achieved disinfection dose, and to compare the achieved disinfection dose with information representing a set disinfection dose, and to discontinue the disinfection if the achieved disinfection dose equals or exceeds the set disinfection dose.

Clause 2. A Water System according to clause 1 wherein the control unit further comprises a memory and the control unit is further configured to store information representing the time required to achieve at least one disinfection dose in the memory during and/or after disinfection has been completed.

Clause 3. A Water System according to clause 2 wherein the control unit is further configured to receive and/or retrieve information representing a set completion time for the next disinfection, and to calculate the time when the next disinfection should be started in order to achieve the disinfection by the set completion time based on information retrieved from the memory representing time required to achieve at least one disinfection dose as stored during or after the completion of an earlier disinfection, and to start the disinfection at the calculated time.

Clause 4. A Water System according to any one of the preceding clauses, wherein the achieved disinfection dose, $A_{0\_achieved}$, is calculated directly or indirectly from the formula:

$$A_{0\_achieved} = \Sigma 10^{[(T-80)/z]} \times \Delta t$$

where z is 10° C., t is the time interval (in seconds) between measurements by the temperature sensor as controlled by the control unit, and T is the measurements by the temperature sensor (in degrees Celsius) within the time interval.

Clause 5. A Water System according to any one of the preceding clauses, wherein the control unit is further configured to calculate the achieved disinfection dose only taking periods into account when the measured temperature exceeds a set threshold temperature.

Clause 6. A Water System according to any one of the preceding clauses, wherein the actuator comprises at least one of the group of a valve and a pump.

Clause 7. A Water System according to any one of the preceding clause, wherein the control unit is further configured to discontinue disinfection by controlling the heating unit to turn off or reduce heating, and/or controlling a valve to close and/or controlling a pump to stop or slow down.

Clause 8. A Water System according to any one of the preceding clauses wherein the fluid path is or, on command from the control unit, can be set as a fluid circuit where the end of the fluid path connects to a return inlet (113) and the water is circulated in the fluid circuit at least during disinfection.

Clause 9. A Water System according to any one of the preceding clauses wherein the temperature sensor is located at the end of the fluid path.

Clause 10. A Water System according to any one of the preceding clauses wherein the control unit is configured to calculate the achieved disinfection dose based on the read temperature.

Clause 11. A Water System according to any one of the preceding clauses wherein the control unit is configured to repeatedly read the temperature as measured by the temperature sensor during the disinfection, calculate the achieved disinfection dose, and compare the achieved disinfection dose with information representing the set disinfection dose until the achieved disinfection dose equals or exceeds the set disinfection dose.

Clause 12. A Water System according to any one of the preceding clauses wherein the controller is configured to provide for that the heated water, which is enabled to flow to the outlet and further into the fluid path, has a temperature which varies during the thermal disinfection.

Clause 13. Medical equipment (400) comprising a fluid path, said fluid path at least partly consisting of a fluid path with a need for regular thermal disinfection (480, 422), the medical equipment further comprising:
an inlet (428) adapted to receive fluid;
an actuator (442, 430) configured to control the flow of the fluid from the inlet to a connector (481), the connector being configured to connect to the fluid path with a need for regular disinfection;
a temperature sensor (450) configured to measure the temperature of the fluid in the fluid path;
a control unit (460) connected to the actuator and the temperature sensor, the control unit being configured to control the fluid flow by means of the actuator, and to read the temperature measured by the temperature sensor;
characterized in that
the control unit is configured to receive and/or retrieve information representing a set disinfection dose; and
the control unit is configured to start the disinfection of the fluid path to be disinfected by controlling the actuator to enable fluid from the inlet to flow to the connector and further into the fluid path with a need for regular disinfection; and the control unit is configured to read the temperature as measured by the temperature sensor during disinfection, and to calculate an achieved disinfection dose, and to compare the achieved disinfection dose with the set disinfection dose, and to discontinue an ongoing disinfection if the achieved disinfection dose equals or exceeds the set disinfection dose.

Clause 14. Medical equipment according to clause 13 further comprising a heating unit (410) configured to heat the fluid received from the inlet and to provide the heated fluid to the inlet of the actuator, and the control unit is further configured to control the heating of the heating unit whereby the heating unit heats the fluid at least for periods when disinfection is ongoing.

Clause 15. Medical equipment according to any one of clause 13 to clause 14 wherein the control unit further comprises a memory and the control unit is further configured to store information representing the time required to achieve at least one disinfection dose in the memory during and/or after disinfection has been completed.

Clause 16. Medical equipment according to clause 15 wherein the control unit further configured to receive and/or retrieve information representing a set completion time for the next disinfection, and to calculate the time when the next disinfection should be started in order to achieve the disinfection by the set completion time based on information retrieved from the memory representing time required to achieve at least one disinfection dose as stored during or after the completion of an earlier disinfection, and to start the disinfection at the calculated time.

Clause 17. Medical equipment according to any one of clause 13 to clause 16, wherein the achieved disinfection dose, $A_{0\_achieved}$, is calculated directly or indirectly from the formula:

$$A_{0\_achieved} = \Sigma 10^{[(T-80)/z]} \times \Delta t$$

where z is 10° C., t is the time interval (in seconds) between measurements by the temperature sensor as controlled by the control unit, and T is the measurements by the temperature sensor (in degrees Celsius) within the time interval.

Clause 18. Medical equipment according to any one of clause 13 to clause 17, wherein the control unit is further configured to calculate the achieved disinfection dose only based on periods when the measured temperature exceeds a set threshold temperature.

Clause 19. Medical equipment according to any one of clause 13 to clause 18, wherein the actuator comprises at least one of the group of a valve and a pump.

Clause 20. Medical equipment according to any one of clause 13 to clause 19, wherein the control unit is further configured to discontinue disinfection by controlling a valve to close and/or controlling a pump to stop or slow down.

Clause 21. Medical equipment according to any one of clause 14 to clause 20, wherein the control unit is further configured to discontinue disinfection by controlling the heating unit to turn off or reduce heating.

Clause 22. Medical equipment according to any one of clause 13 to clause 21, wherein the medical equipment is configured to receive water as the fluid.

Clause 23. Medical equipment according to any one of clause 13 to clause 22, wherein the fluid path with a need for regular disinfection is or, on command from the control unit, can be set as a fluid circuit in which fluid is circulated at least during disinfection.

Clause 24. Medical equipment according to any one of clause 13 to clause 23 wherein the temperature sensor is located at the end of the fluid path.

Clause 25. Medical equipment according to any one of clause 13 to clause 24, wherein the medical equipment is a dialysis apparatus and the fluid path to be disinfected is the treatment fluid path of the dialysis apparatus.

Clause 26. Medical equipment according to any one of clause 13 to clause 25, wherein the control unit is configured to calculate the achieved disinfection dose based on the read temperature.

Clause 27. A Medical equipment according to any one of according to any one of clause 13 to clause 26 wherein the control unit is configured to repeatedly read the temperature as measured by the temperature sensor during the disinfection, calculate the achieved disinfection dose, and compare the achieved disinfection dose with information representing the set disinfection dose until the achieved disinfection dose equals or exceeds the set disinfection dose.

Clause 28. A Medical equipment according to any one of clause 13 to clause 27 wherein the controller is configured to provide for that the fluid, which is enabled to flow to the connector and further into the fluid path, has a temperature which varies during the thermal disinfection.

Clause 29. A method for performing thermal disinfection of a fluid path, the method comprising the steps of:
  i) receiving at an inlet a fluid to be used during disinfection of the fluid path to be disinfected;
  ii) heating the fluid received from the inlet;
  iii) setting a disinfection dose;
  iv) starting the thermal disinfection by controlling an actuator thereby enable heated fluid from the heating unit to flow into the fluid path to be disinfected;
  v) measuring the temperature of the fluid in the fluid path to be disinfected;
  vi) calculating an achieved disinfection dose;
  vii) comparing the achieved disinfection dose with the set disinfection dose; and
  viii) discontinuing the disinfection if the achieved disinfection dose equals or exceeds the set disinfection dose.

Clause 30. A method according to clause 29 wherein steps v) to vii) are repeated until the achieved disinfection dose equals or exceeds the set disinfection dose.

Clause 31. A method according to any one of clause 29 and clause 30 further comprising the steps of:
  ai) setting a completion time;
  aii) storing information in a memory representing the time required to achieve at least one disinfection dose;
  aiii) calculating the time when the disinfection should be started in order to achieve the disinfection by the set completion time by deducting a stored required time for the set disinfection dose from the set completion time; and
  aiv) starting the disinfection at the time calculated in step aiii).

Clause 32. A method according to any one of clause 29 to clause 31 wherein the achieved disinfection dose, $A_{0\_achieved}$, is calculated directly or indirectly from the formula:

$$A_{0\_achieved} = \Sigma 10^{[(T-80)/z]} \times \Delta t$$

where z is 10° C., t is the time interval (in seconds) between measurements by the temperature sensor as controlled by the control unit, and T is the measurements by the temperature sensor (in degrees Celsius) within the time interval.

Clause 33. A method according to any one of clause 29 to clause 32 wherein the achieved disinfection dose only is calculated based on periods when the measured temperature exceeds a set threshold temperature.

Clause 34. A method according to any one of clause 29 to clause 33 wherein the step of discontinuing the disinfection comprises the steps of turning off or reducing the heating of the fluid received from the inlet, and/or controlling a valve to close and/or controlling a pump to stop or slow down.

Clause 35. A method according to any one of clause 29 to clause 34, further comprising the step of providing the fluid of the inlet to the outlet during periods when disinfection is not being performed.

Clause 36. A method according to any one of clause 29 to clause 35 wherein the step of calculating an achieved disinfection dose is based on the measured temperature.

Clause 37. A method according to any one of clause 29 to clause 36 further comprising the step of providing for that the heated fluid has a temperature which varies during the thermal disinfection.

Clause 38. An apparatus (110, 320, 400) for thermal disinfection of a fluid path, the apparatus comprising:
- an inlet (113, 321, 428) for receiving a fluid to be used during disinfection of the fluid path;
- a heating unit (115, 325, 410) connected to the inlet and configured to heat the fluid received from the inlet;
- an actuator (117, 122, 324, 442, 430) connected to the heating unit and configured to control the flow of the fluid from the heating unit to an outlet (112, 322, 425), the outlet being configured to connect to the fluid path to be disinfected;
- a temperature sensor (118, 358, 450) configured to measure the temperature of the fluid in the fluid path;
- a control unit (119, 319, 460) connected to the actuator and the temperature sensor, the control unit being configured to control the fluid flow by means of the actuator, and to read the temperature measured by the temperature sensor;

characterized in that
the control unit is configured to receive information representing a set disinfection dose;
the control unit is configured to start the disinfection of the fluid path to be disinfected by controlling the actuator to enable fluid from the heating unit to flow to the outlet and further into the fluid path to be disinfected; and
the control unit is configured to read the temperature as measured by the temperature sensor during the disinfection, and to calculate the achieved disinfection dose, and to compare the achieved disinfection dose with the set disinfection dose, and to discontinue the disinfection if the achieved disinfection dose equals or exceeds the set disinfection dose.

Clause 39. An apparatus according to clause 38 wherein the control unit further comprises a memory and the control unit is further configured to store information representing the time required to achieve at least one disinfection dose in the memory during and/or after disinfection has been completed.

Clause 40. An apparatus according to clause 38 or clause 39 wherein the control unit is further configured to receive and/or retrieve information representing a set completion time for the next disinfection, and to calculate the time when the next disinfection should be started in order to achieve the disinfection by the set completion time based on information retrieved from the memory representing time required to achieve at least one disinfection dose as stored during or after the completion of an earlier disinfection, and to start the disinfection at the calculated time.

Clause 41. An apparatus according to any one of clause 38 to clause 40, wherein the achieved disinfection dose, $A_{0\_achieved}$, is calculated directly or indirectly from the formula:

$$A_{0\_achieved} = \Sigma 10^{[(T-80)/z]} \times \Delta t$$

where z is 10° C., t is the time interval (in seconds) between measurements by the temperature sensor as controlled by the control unit, and T is the measurements by the temperature sensor (in degrees Celsius) within the time interval.

Clause 42. An apparatus according to any one of clause 38 to clause 41, wherein the control unit is further configured to calculate the achieved disinfection dose only based on periods when the measured temperature exceeds a set threshold temperature.

Clause 43. An apparatus according to any one of clause 38 to clause 42, wherein the actuator comprises at least one of the group of a valve and a pump.

Clause 44. An apparatus according to any one of clause 38 to clause 43, wherein the control unit is further configured to discontinue disinfection by controlling the heating unit to turn off or reduce heating, and/or controlling a valve to close and/or controlling a pump to stop or slow down.

Clause 45. An apparatus according to any one of clause 38 to clause 44, further comprising a filtering unit configured to filter the incoming fluid and to provide it to the outlet at least during periods when disinfection is not being performed.

Clause 46. An apparatus according to any one of clause 38 to clause 45, wherein the apparatus is configured to receive water as the fluid.

Clause 47. An apparatus according to any one of clause 38 to clause 46 wherein the control unit is configured to calculate the achieved disinfection dose based on the read temperature.

Clause 48. An apparatus according to any one of clause 38 to clause 47 wherein the control unit is configured to repeatedly read the temperature as measured by the temperature sensor during the disinfection, calculate the achieved disinfection dose, and compare the achieved disinfection dose with information representing the set disinfection dose until the achieved disinfection dose equals or exceeds the set disinfection dose.

Clause 49. An apparatus according to any one of clause 38 to clause 48 wherein the controller is configured to provide for that the fluid, which is enabled to flow to the outlet and further into the fluid path to be disinfected, has a temperature which varies during the thermal disinfection.

An advantage, in respect of at least some embodiments of the present invention, is that energy consumption is lowered compared to conventional disinfection processes, which in turn leads to a disinfection process which puts less load on the environment. Furthermore, the time needed to perform disinfection is reduced which in turn leads to that the available time to treat patients can be increased.

The expression "and/or" as used in the present application and claims refers to multiple embodiments of the present invention representing embodiments with the capability of performing both alternatives on either side of the expression as well as individual embodiments capable of performing only one of the alternatives on either side of the expression.

The invention claimed is:
1. A water system for providing water to at least one connected device through a fluid path and being able to disinfect the fluid path by means of thermal disinfection, the water system comprising:

an inlet for receiving water to the water system;
a heating unit configured to heat water within the water system;
a filter unit configured to filter water within the water system in order to provide filtered water to an outlet;
an actuator configured to control the flow of the water from the heating unit to the outlet;
a fluid path connected to the outlet, the fluid path comprising at least one connector configured to connect to at least one device to which water is provided by the water system;
a temperature sensor configured to measure the temperature of the fluid in the fluid path; and
a control unit including a memory and connected to the heating unit, the actuator and the temperature sensor, the control unit configured to (i) start the disinfection of the fluid path by controlling the heating unit to heat water and controlling the actuator to enable heated water to flow to the outlet and further into the fluid path, (ii) read the temperature as measured by the temperature sensor during the disinfection, (iii) calculate an achieved disinfection dose based on the read temperature, (iv) compare the achieved disinfection dose with information representing a set disinfection dose, (v) discontinue the disinfection if the achieved disinfection dose equals or exceeds the set disinfection dose, and (vi) store information representing a time required for the achieved disinfection dose to equal or exceed the set disinfection dose in the memory during and/or after disinfection has been completed.

2. A water system according to claim 1 wherein the temperature sensor is located at or near a location of the fluid path that experiences a lowest temperature of the heated water during thermal disinfection, which ensures that a disinfection dose provided elsewhere in the fluid path is at or above the achieved disinfection dose.

3. A water system according to claim 1 wherein the control unit is further configured to receive and/or retrieve information representing a set completion time for the next disinfection, and to calculate the time when the next disinfection should be started in order to achieve the disinfection by the set completion time based on information retrieved from the memory representing the time required for the achieved disinfection dose to equal or exceed the set disinfection dose, and to start the disinfection at the calculated time.

4. A water system according to claim 1, wherein the achieved disinfection dose, A0_achieved, is calculated directly or indirectly from the formula:

$$A0\_achieved = \Sigma 10^{[(T-80)/z]} \times \Delta t$$

where z is 10° C., t is the time interval (in seconds) between measurements by the temperature sensor as controlled by the control unit, and T is at least one measurement by the temperature sensor (in degrees Celsius) within the time interval.

5. Medical equipment comprising a fluid path, at least a portion of said fluid path having a need for regular thermal disinfection, the medical equipment further comprising:
an inlet adapted to receive fluid;
an actuator configured to control the flow of the fluid from the inlet to a connector, the connector being configured to connect to the portion of the fluid path having a need for regular disinfection;
a temperature sensor configured to measure the temperature of the fluid in the fluid path; and
a control unit including a memory and connected to the actuator and the temperature sensor, the control unit configured to (i) receive and/or retrieve information representing a set disinfection dose, (ii) start the disinfection of the fluid path to be disinfected by controlling the actuator to enable fluid from the inlet to flow to the connector and further into the portion of the fluid path having a need for regular disinfection, (iii) read the temperature as measured by the temperature sensor during disinfection, (iv) calculate an achieved disinfection dose based on the read temperature, (v) compare the achieved disinfection dose with the set disinfection dose, (vi) discontinue an ongoing disinfection if the achieved disinfection dose equals or exceeds the set disinfection dose, and (vii) store information representing a time required for the achieved disinfection dose to equal or exceed the set disinfection dose in the memory during and/or after disinfection has been completed.

6. Medical equipment according to claim 5 further comprising a heating unit configured to heat the fluid received from the inlet and to provide the heated fluid to the actuator, and wherein the control unit is further configured to control the heating of the heating unit to heat the fluid at least for periods when disinfection is ongoing.

7. Medical equipment according to claim 5 wherein the temperature sensor is located at or near a location of the fluid path that experiences a lowest temperature of the fluid during thermal disinfection, which ensures that a disinfection dose provided elsewhere in the fluid path is at or above the achieved disinfection dose.

8. Medical equipment according to claim 5 wherein the control unit is further configured to receive and/or retrieve information representing a set completion time for the next disinfection, and to calculate the time when the next disinfection should be started in order to achieve the disinfection by the set completion time based on information retrieved from the memory representing the time required for the achieved disinfection dose to equal or exceed the set disinfection dose, and to start the disinfection at the calculated time.

9. Medical equipment according to claim 5, wherein the achieved disinfection dose, A0_achieved, is calculated directly or indirectly from the formula:

$$A0\_achieved = \Sigma 10^{[(T-80)/z]} \times \Delta t$$

where z is 10° C., t is the time interval (in seconds) between measurements by the temperature sensor as controlled by the control unit, and T is the measurements by the temperature sensor (in degrees Celsius) within the time interval.

10. A method for performing thermal disinfection of a fluid path, the method comprising the steps of:
i) receiving at an inlet a fluid to be used during disinfection of the fluid path to be disinfected;
ii) heating the fluid received from the inlet;
iii) setting a disinfection dose;
iv) starting the thermal disinfection by controlling an actuator to thereby enable the heated fluid to flow into the fluid path to be disinfected;
v) measuring the temperature of the heated fluid in the fluid path;
vi) calculating an achieved disinfection dose based on the measured temperature;
vii) comparing the achieved disinfection dose with the set disinfection dose;

viii) discontinuing the disinfection if the achieved disinfection dose equals or exceeds the set disinfection dose; and vix) storing in a memory information representing a time required for the achieved disinfection dose to equal or exceed the set disinfection dose during and/or after disinfection has been completed.

11. A method according to claim 10 wherein steps v) to vii) are repeated until the achieved disinfection dose equals or exceeds the set disinfection dose.

12. A method according to claim 10 further comprising the steps of:
ai) setting a completion time;
aii) calculating the time when the disinfection should be started in order to achieve the disinfection by the set completion time by deducting the time required for the achieved disinfection dose to equal or exceed the set disinfection dose from the set completion time; and
aiii) starting the disinfection at the time calculated in step aii).

13. A method according to claim 10 wherein the achieved disinfection dose, A0_achieved, is calculated directly or indirectly from the formula:

$$A0\_achieved = \Sigma 10^{[(T-80)/z]} \times \Delta t$$

where z is 10° C., t is the time interval between measurements by the temperature sensor as controlled by the control unit, and T is the measurements by the temperature sensor within the time interval.

14. An apparatus for thermal disinfection of a fluid path, the apparatus comprising:
an inlet for receiving a fluid to be used during disinfection of the fluid path;
a heating unit connected to the inlet and configured to heat the fluid received from the inlet;
an actuator connected to the heating unit and configured to control the flow of the fluid from the heating unit to an outlet, the outlet being configured to connect to the fluid path to be disinfected;
a temperature sensor configured to measure the temperature of the fluid; and
a control unit including a memory and connected to the actuator and the temperature sensor, the control unit configured to (i) receive information representing a set disinfection dose, (ii) start the disinfection of the fluid path to be disinfected by controlling the actuator to enable fluid from the heating unit to flow to the outlet and further into the fluid path to be disinfected, (iii) read the temperature as measured by the temperature sensor during the disinfection, (iv) calculate an achieved disinfection dose based on the read temperature, (v) compare the achieved disinfection dose with the set disinfection dose, (vi) discontinue the disinfection if the achieved disinfection dose equals or exceeds the set disinfection dose, and (vii) store information representing a time required for the achieved disinfection dose to equal or exceed the set disinfection dose in the memory during and/or after disinfection has been completed.

15. An apparatus according to claim 14 wherein the temperature sensor is located at or near a location of the fluid path that experiences a lowest temperature of the fluid during thermal disinfection, which ensures that a disinfection dose provided elsewhere in the fluid path is at or above the achieved disinfection dose.

16. An apparatus according to claim 14 wherein the control unit is further configured to receive and/or retrieve information representing a set completion time for the next disinfection, and to calculate the time when the next disinfection should be started in order to achieve the disinfection by the set completion time based on information retrieved from the memory representing the time required for the achieved disinfection dose to equal or exceed the set disinfection dose, and to start the disinfection at the calculated time.

17. An apparatus according to claim 14, wherein the achieved disinfection dose, A0_achieved, is calculated directly or indirectly from the formula:

$$A0\_achieved = \Sigma 10^{[(T-80)/z]} \times \Delta t$$

where z is 10° C., t is the time interval between measurements by the temperature sensor as controlled by the control unit, and T is the measurements by the temperature sensor within the time interval.

18. An apparatus according to claim 14, wherein the control unit is further configured to calculate the achieved disinfection dose based only on periods when the measured temperature exceeds a set threshold temperature.

19. An apparatus according to claim 14, wherein the actuator comprises at least one of the group of a valve and a pump.

20. An apparatus according to claim 14, wherein the control unit is further configured to discontinue disinfection by controlling the heating unit to turn off or reduce heating, and/or controlling a valve to close and/or controlling a pump to stop or slow down.

21. A water system according to claim 1, wherein the temperature sensor is located at an end of the fluid path, and wherein the end of the fluid path experiences a lowest temperature during thermal disinfection.

22. A method according to claim 10, which includes measuring the temperature of the fluid in the fluid path at an end of the fluid path, and wherein the end of the fluid path experiences a lowest temperature during thermal disinfection.

23. An apparatus according to claim 14, wherein the temperature sensor is located at an end of the fluid path, and wherein the end of the fluid path experiences a lowest temperature during thermal disinfection.

* * * * *